United States Patent [19]

Nojima

[11] Patent Number: 5,035,367
[45] Date of Patent: Jul. 30, 1991

[54] APPARATUS FOR DISPOSING OF MEDICAL WASTE BY CRUSHING

[75] Inventor: Norihiro Nojima, Tokyo, Japan

[73] Assignees: Nojima Keikinzoku Co., Ltd., Higashimurayama; Kaneto Co., Ltd., Kaminoyama, both of Japan

[21] Appl. No.: 478,574

[22] Filed: Feb. 12, 1990

[30] Foreign Application Priority Data

Feb. 15, 1989 [JP] Japan .................. 1-16472[U]
May 16, 1989 [JP] Japan .................. 1-56358[U]
Dec. 8, 1989 [JP] Japan .................. 1-320048

[51] Int. Cl.⁵ .......................................... B02C 19/14
[52] U.S. Cl. ......................... 241/37.5; 241/73; 241/99; 241/100; 241/101.7; 241/190; 241/243; 241/292.1; 241/DIG. 38
[58] Field of Search .............. 241/101.7, 99, 100, 241/190, 186 A, 34, 195, 37.5, DIG. 38, 243, 73, 246, 247, 89.3, 292.1

[56] References Cited

U.S. PATENT DOCUMENTS

| | | | |
|---|---|---|---|
| 3,240,247 | 3/1966 | Lautzenheiser | 241/190 X |
| 3,412,770 | 11/1968 | Johnson | 241/190 X |
| 3,545,689 | 12/1970 | Luscombe | 241/190 X |
| 3,672,803 | 6/1972 | Rees | 241/186 A X |
| 3,926,379 | 12/1975 | Dryden et al. | 241/99 X |
| 3,929,295 | 12/1975 | Montalbano | 241/190 |
| 4,269,364 | 5/1981 | Moriconi et al. | 241/99 X |
| 4,619,409 | 10/1986 | Harper et al. | 241/99 X |
| 4,759,508 | 7/1988 | Griffith et al. | |

FOREIGN PATENT DOCUMENTS

| | | | |
|---|---|---|---|
| 0054823 | 6/1982 | European Pat. Off. | |
| 363650 | 11/1922 | Fed. Rep. of Germany | 241/243 |
| 662370 | 7/1938 | Fed. Rep. of Germany | 241/243 |
| 2341914 | 2/1975 | Fed. Rep. of Germany | 241/190 |
| 3510830 | 10/1986 | Fed. Rep. of Germany | |
| 1033062 | 8/1983 | U.S.S.R. | 241/190 |

Primary Examiner—Mark Rosenbaum

[57] ABSTRACT

An apparatus for disposing of medical industrial waste by crushing comprises an opening for use in putting the industrial waste therethrough, a door for use in opening and closing the opening, a waste conveyor unit, a crushing unit for crushing the medical industrial waste conveyed by the conveyor unit, a discharging unit for discharging the waste crushed by the crushing unit, a container for storing the crushed waste discharged from the conveyor unit, and a sterilizing unit. The crushing unit includes fixed blades and rotary blades and the crushed material discharged from the crushing unit is stored in the container as the rotary blades rotates.

19 Claims, 6 Drawing Sheets

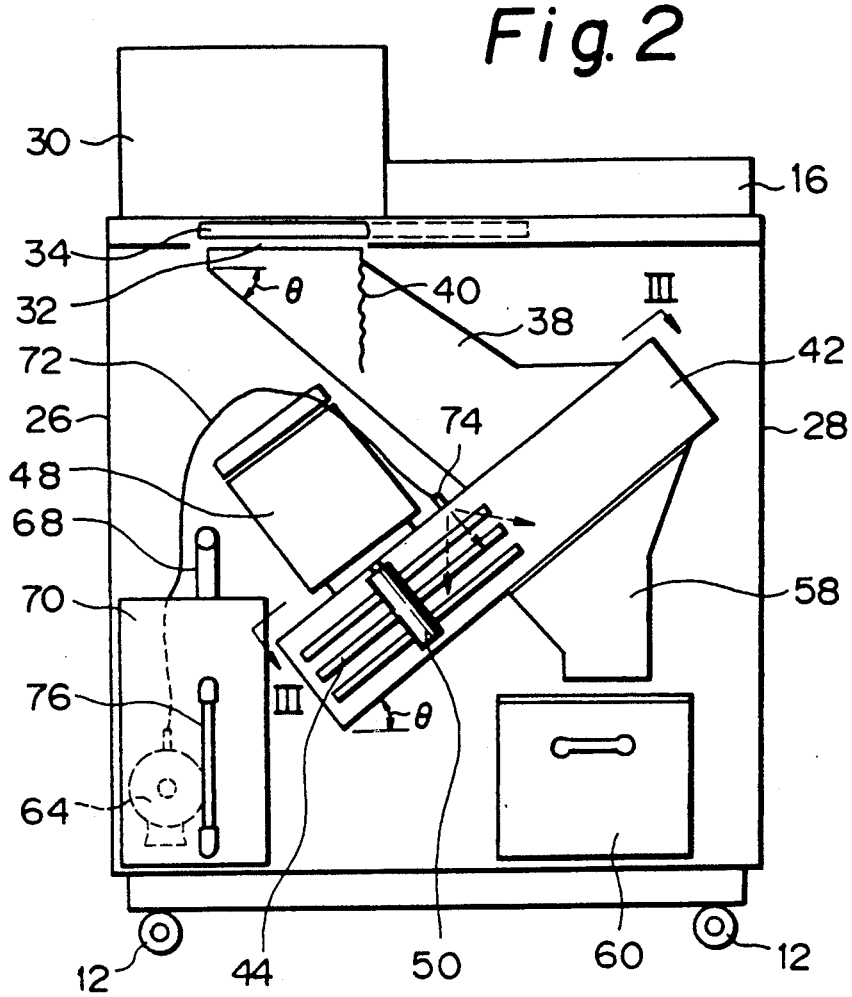
Fig. 2
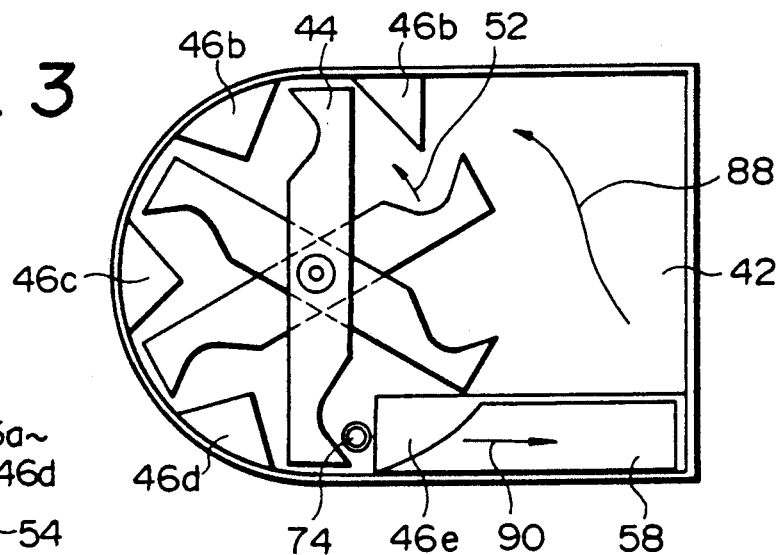
Fig. 3
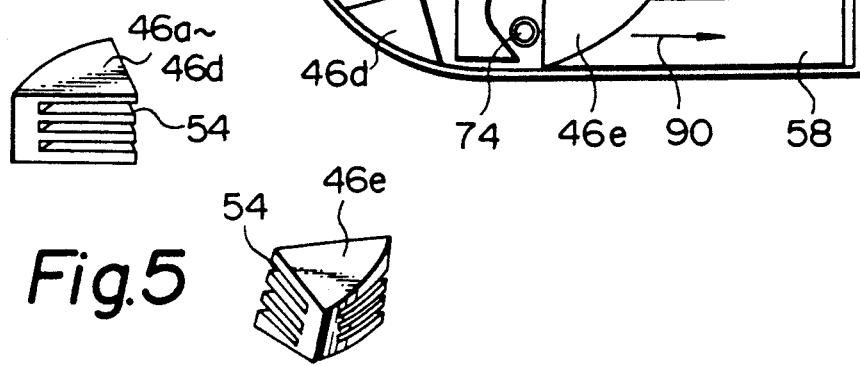
Fig. 4
Fig. 5

APPARATUS FOR DISPOSING OF MEDICAL WASTE BY CRUSHING

BACKGROUND OF THE INVENTION

The present invention relates to an apparatus for disposing of industrial waste, particularly medical waste by crushing.

Heretofore, medical waste such as used hypodermic needles and medical testing instruments have been sterilized or burnt after use as occasion demands before being buried in the ground like industrial waste in general. However, such a disposing method is disadvantageous in that used hypodermic needles, glassware for testing purposes and the like may stick in the fingers of nurses or fall off their hands and broken while being carried to incinerators. Moreover, the medical waste buried in the ground may be forced up the ground before being completely corroded and cause unexpected accidents to men, living things (e.g. dogs and cats), or damage to vehicle tires and the like; in other words, causing secondary disaster.

In addition, the recent mass production of medical wastes tends to make it inevitable to dispose of them immediately after use without subjecting them to pretreatment which should have been made, including sterilizing and burning them. Such countermeasures, however, are led to problems of infection with an apriority immunity anergy syndrome, B-type hepatitis and the like, and have posed a serious social problem.

In view of the foregoing problems, an object of the present invention is to provide an apparatus for disposing of medical waste by crushing such as disposable syringes, hydrodermic needles, FR bottles, Ringer's solution bottles and the like with safety.

Another object of the present invention is to provide a compact lightweight apparatus for simply disposing of medical waste by crushing immediately after use in hospitals or the like.

Still another object of the present invention is to provide the aforementioned apparatus that can be movable to any place readily with safety.

Still another object of the present invention is to provide an apparatus for disposing of used medical devices simply and quickly by crushing, the medical devices including those having residual liquid and blood, to say nothing of empty ones.

These and other objects of the invention will become more apparent in the detailed description and examples which follow.

BRIEF DESCRIPTION OF THE DRAWINGS

FIG. 2 is a diagram illustrating the internal construction of the apparatus of FIG. 1.

FIG. 3 is a diagram taken on line III—III of FIG. 2.

FIGS. 4 and 5 are diagrams illustrating fixed blades.

DESCRIPTION OF THE PREFERRED EMBODIMENT

Figure 1:
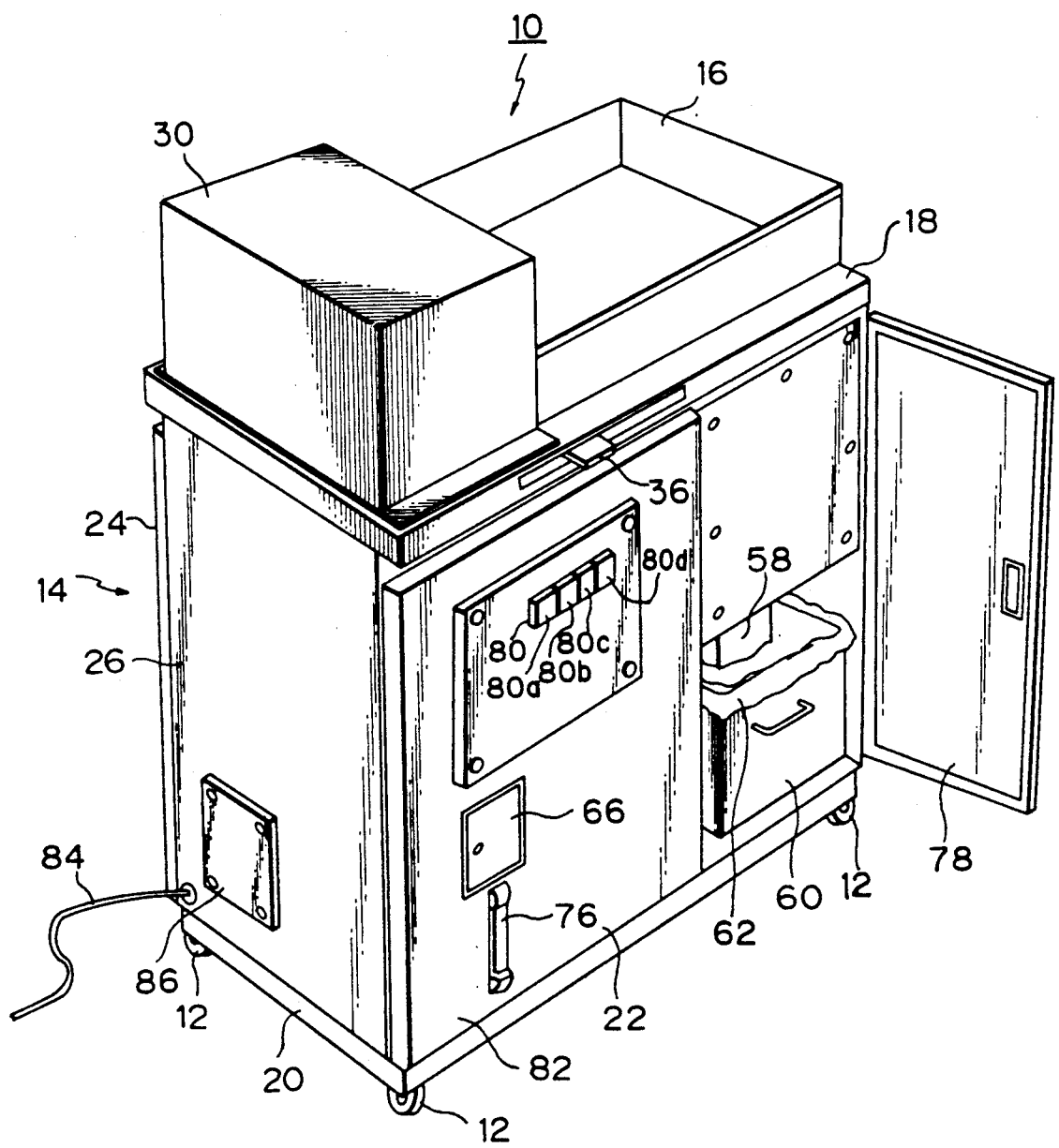
FIG. 1 is an overall perspective view of an apparatus for disposing of medical waste by crushing as a first embodiment of the present invention.

FIG. 1 is an overall perspective view of an apparatus for disposing of waste by crushing according to the present invention. The apparatus 10 embodying the present invention comprises a body 14 movably supported by casters 12. The body 14 has a top cover 18 holding a hopper 16 for accommodating waste, a bottom cover 20, a front cover 22 having operating buttons, a rear cover 24 opposite to the front cover, and side covers 26, 28.

The hopper 16 is a box for accommodating medical waste to be disposed of and has a drop-in hole formed in part of the bottom cover. A safety dust-proof detachable cover 30 is preferably installed above the drop-in hole to cover part of the hopper 16 so that crushed material is prevented from flying out of the apparatus 10 during the crushing operation or hitting the operator.

An opening 32 matching the drop-in hole in the underside of the hopper is formed in the top cover. This opening 32 can be opened and closed by a longitudinally movable damper 34. The damper 34 can be manipulated by means of a damper handle 36 protruding from the top cover 18 toward the front cover 22.

Right below the opening 32 is a sucking hopper guide 38 downwardly tilted to the right by an angle of $\theta$ (preferably about 60° with respect to the horizontal plane (see FIG. 2). A check plate 40 made of, e.g. rubber is hanged down from the upper end of the tilted guide 38 to check the back flow of the material being processed. Moreover, a crusher chamber 42 communicates with the lower end of the guide, the crusher chamber being tilted likewise from the upper right-hand side to the lower left-hand side by an angle of $\theta$ (preferably about 60°) with respect to the horizontal plane.

The crusher chamber 42 comprises an upper portion incorporated with the lower end portion of the tilted guide 38 and used for guiding the waste, and a lower portion provided with rotary blades 44 and fixed blades 46. The rotary blades 44 are rotated by a rotary shaft 50 of a motor 48 in direction of arrow 52. Although the number of rotary blades 44 is shown to be three, it is needless to say not limited thereto. Each of the blades 44 has a front end which is indented and/or twisted to positively introduce the waste to the fixed blade 46. As shown in FIG. 3, five fixed blades 46a–46e are secured to the lower portion of the crusher chamber 42. Each of the fixed blades is, as shown in FIG. 4, provided with a predetermined number of grooves 54 through which the rotary blades pass. An opening 56 for use in discharging the crushed waste is provided on the rear side of the last fixed blade 46e and also communicates with a discharge port 58 for use in discharging the crushed waste outside. As shown in FIG. 1, a container box 60 for receiving the crushed waste is placed under the discharge port 58, so that the waste crushed to pieces is dumped into the box. A vinyl bag 62 or the like is normally put into the box 60 to facilitate the discarding of the contents.

A sterilizing unit is installed in the apparatus according to the present invention for disposing of medical supplies with safety. More specifically, a pump 64 for supplying an antiseptic solution is provided inside the front cover 22 of FIG. 1 as shown in FIG. 2. The pump 64 is used to sent a jet of antiseptic solution via a pipe 72 to a jet orifice of the crusher chamber 42, the antiseptic solution being injected from an injection port 68 into an antiseptic solution tank 70 by opening a door 66 in the front cover 22. A liquid level gauge 76 on the front cover makes possible observation from the outside.

The front cover 22 consists of a door 78 for use when the crushed waste is taken out, a fixed wall 82 accommodating an array of operating buttons 80 and the door 66. A power supply lead 84, a pump service port 86 and the like are provided on the side cover 26.

Before the above-described apparatus is operated, waste to be crushed such as used hypodermic needles, syringes and the like is put into the hopper 16. The button 80a is subsequently pressed to start the motor 48; however, the order may be reversed. An operator in charge then opens the opening 32 by operating the damper handle 36, letting the waste in the hopper 16 fall into the opening 32 using a push rod, for instance. The waste that has fallen into the opening 32 keep falling successively along the tilted guide 38. When the waste reaches the crusher chamber 42, it is caused to turn to flow in direction of arrow 88 and enters the blade section. The rotary blades 44 lead the waste to the fixed blades 46 where it is crushed; pressure-crushing and the like take place between the rotating rotary blades 44 and the grooves 54 of the fixed blades 46 in this case. The centrifugal force resulting from the rotation of the rotary blades 44 compels the whole waste to pass along the fixed blades 46. The waste subjected to crushing operations in four steps as illustrated is sterilized by an antiseptic solution, crushed again, discharged from the opening 56 on the rear side of the fixed blade 46e in direction of arrow 90 toward the discharge port 58, and discarded into the bag 62 of the container box 60. At a point of time crushing sound stops after the waste has been fed totally, the crushing operation is completed. The container box 60 is then taken out of the apparatus 10 by gripping a handle 88 and the bag 62 is then pulled out of the box 60 to dispose of the waste thus cut to pieces like ordinary industrial waste. The bag may be disposed of when it becomes full of the waste. As the medical waste is cut to pieces and sterilized, there is no risk of causing secondary disaster. When the button 80b is pressed, all functions are suspended. As the button 80c lights when the deficiency of the antiseptic solution occurs, it can be used simultaneously as the liquid level gauge. Moreover, the button 80d is an antiseptic solution jet button and, when it is pressed once, a jet of antiseptic solution is sent out for 30 seconds. When the button 80d is pressed again, its switch is opened to stop jetting out the solution. Alternatively, these buttons may be replaced with some other mechanisms. While the apparatus 10 is held in an ON state, it may be cleansed by running a disinfectant from the hopper 16.

Examples of medical supplies that can be crushed by the apparatus include hypodermic needles, syringes, glass bottles for containing Ringer's solution, ampules, bottles for any other medical use, etc.

FIGS. 6-10 show a second embodiment of the present invention.

Figure 6:
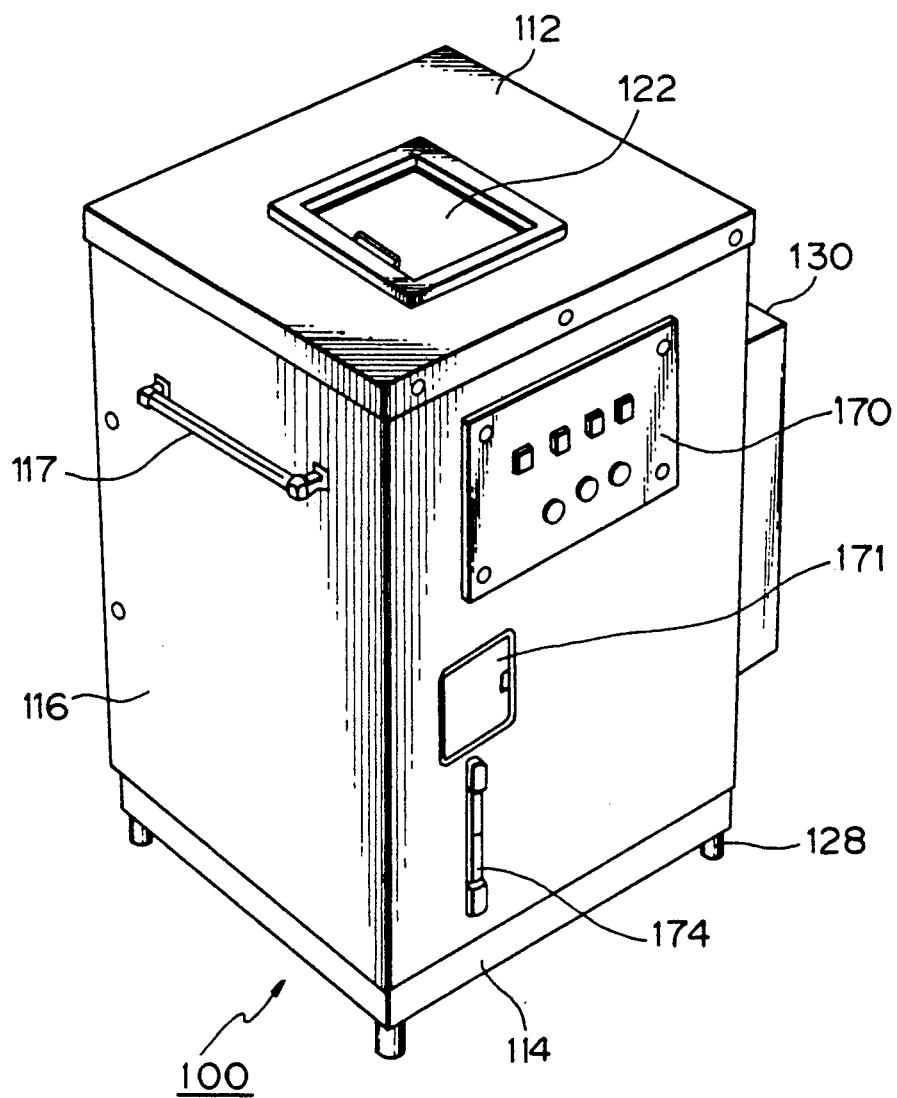
FIG. 6 is an overall perspective view of an apparatus for disposing of medical waste by crushing according to the present invention as a second embodiment.
Figure 7:
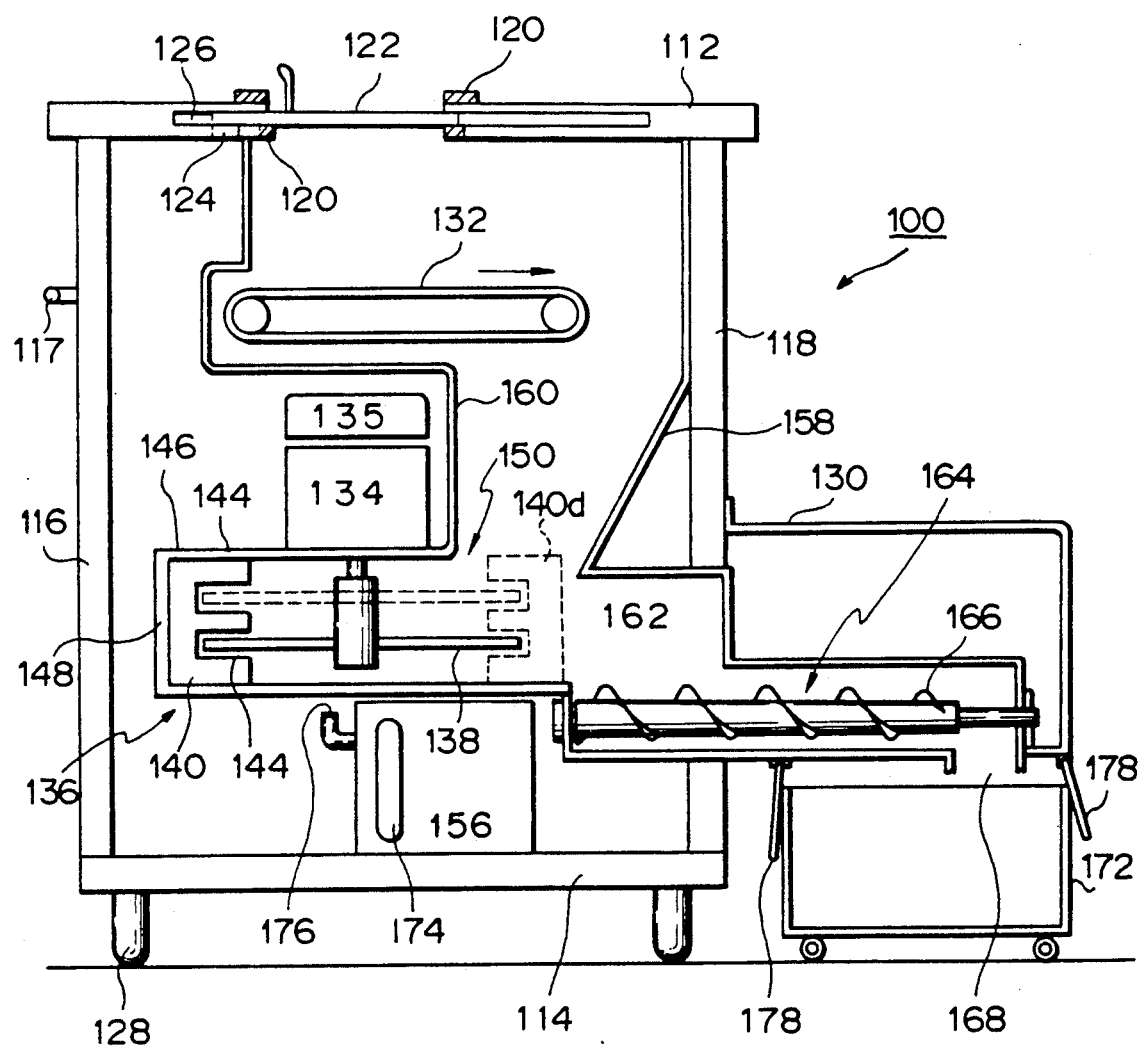
FIG. 7 is an elevational sectional view of the apparatus of FIG. 6.

FIG. 6 is an overall perspective view of another apparatus for disposing of waste by crushing according the present invention. FIG. 7 is a schematic sectional view of the apparatus. This apparatus 100 has an upper cover 112, a bottom cover 114, left- and right-hand side walls, a front wall, and a rear wall.

The upper cover 112 is provided with an opening 120 having a predetermined dimension in its substantially central portion, the opening 120 forming an inlet for used devices to be disposed of. The opening 120 is supplied with, e.g. a slidable door 122, which is so arranges as to readily be opened and closed by the operator. The opening 120 is preferably equipped with a magnetic catch 124 for holding the door 122 in a closed state and further a limit switch 126 for sensing the switching state of the door 122. Needless to say, the hopper 16 of FIG. 1 may be fitted to the upper cover 112.

Casters 128 are attached to the bottom cover 114 so that the apparatus 100 may freely be moved.

A discharge chamber 130 for accommodating crushed waste is provided on the side wall 118 on one side, whereas a pushing rod 117 for use in moving the apparatus 100 is fitted to the side wall 116 on the other.

A feed conveyor 132 is provided under the opening 120 of the upper cover in the apparatus 110. The conveyor 132 is interlocked with the limit switch 126 and operated only when the switch senses that the door 122 has been closed. The conveyor 132 has an area substantially greater than that of the opening 120 and prevents the operator from inadvertently thrusting his fingers beyond the conveyor and simultaneously the waste crushed by an crushing unit, which will be described later, from flying out of the apparatus 100 via the opening 120.

A motor 124 rotating at 1,800 r.p.m. is installed under the feed conveyor 132. The motor 134 is the one which is well known and used for starting the feed conveyor 132 via a reducer 135. The motor 134 is also used for rotating rotors 138 of a crushing unit 136 provided under the motor 134.

Figure 8:
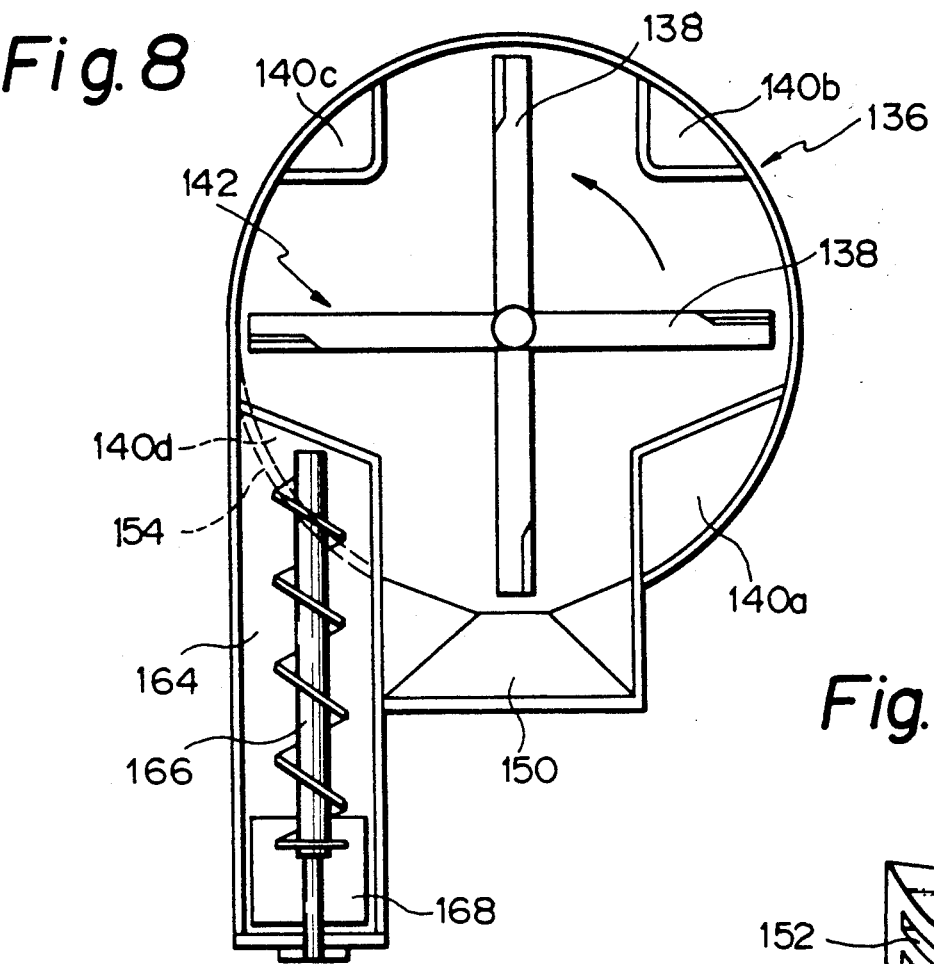
FIG. 8 is a top view of the internal construction of the crushing unit.

The crushing unit 136 schematically shown in FIG. 8 includes four fixed blades 140 (140a-140d) spaced, e.g. 90 degrees apart form one another and rotary blades 142 formed on a pair of rotors 138 so arranges that they cross at right angles and rotated by the motor 134. The front end of each rotor 138 is preferably twisted so as to press the waste against the bottom side of the crushing unit 136.

Figure 10:
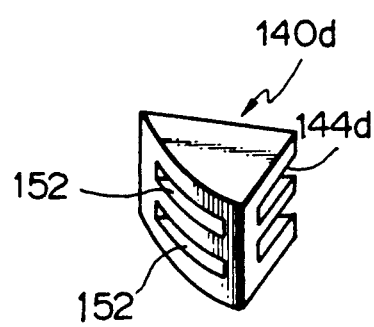
FIG. 10 is a schematic perspective view of the fourth fixed blade.
Figure 9:
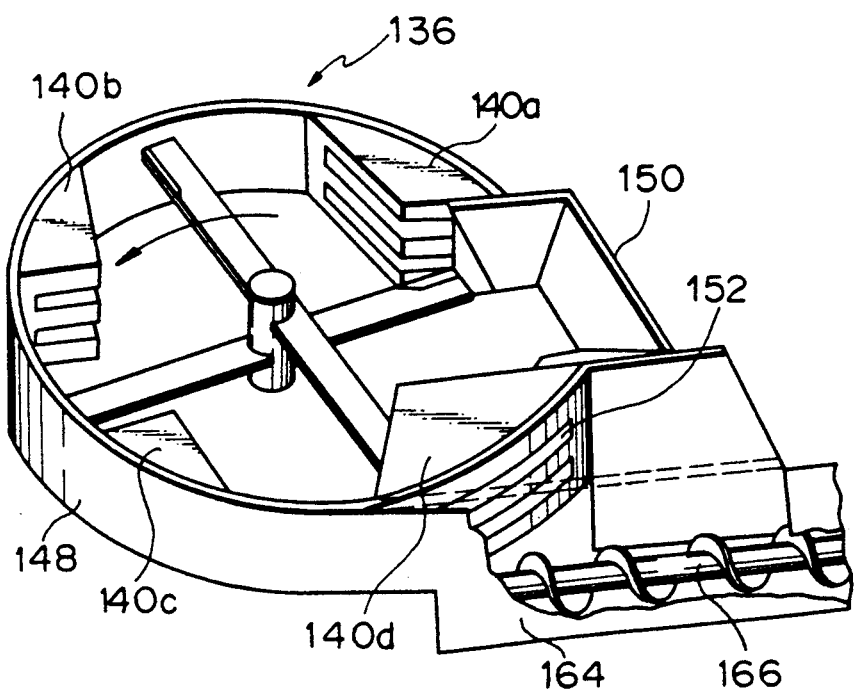
FIG. 9 is a perspective view of the top of the partially exploded crushing unit.

Each of the fixed blades 140 is, as shown in FIG. 7, provided with a pair of vertically arranged grooves 144 for allowing the rotors 138 to pass therethrough. Moreover, the grooves 144d of the fixed blade 140d are perforated in the central portion of the blade to form slits 152. As is well known to those skilled in the art, the fixed blades 140a-140d may be formed of a pair of plate-like steel members formed to shape and stacked with a spacer therebetween or of a steel block processed to shape as shown in FIG. 10. In other words, there are variations of the fixed blade to be made in compliance with design requirements depending on the dimension, number and angle of the rotor to be arranged, the dimension, number and angle of the fixed blade, the number of grooves, the configuration of an opening and the like. The rotors and the fixed blades may be replaced with those most suitable, depending on the waste to be disposed of.

The crushing unit 136 has a worktop 146 thereon and a cylindrical wall 148 surrounding the rotors.

Part of the cylindrical wall 148 has a diameter radially outwardly extended to form an extension 150. The extension is situated between the first fixed blade 140a and the fourth fixed blade 140d and serves as an inlet for the waste. Further, an opening 154 is provided in part of the cylindrical wall 148. The rear side of the fourth fixed blade 140d communicates with the opening 154, for instance, as shown in FIG. 10. The centrifugal force generated by the rotors 138 compels the crushed waste to be forced out of the opening 154 tangentially via the opening 152. There is preferably provided a tank and a supply unit 156 for receiving an antiseptic solution and supplying the crushing unit 136 with the solution between the lower portion of the crushing unit 136 and the bottom cover 114.

A guide plate 158 for guiding the waste fed by the feed conveyor 132 to the inlet for the waste in the crushing unit is provided within the apparatus 100. Moreover, a wall plate 160 is provided opposite to the guide plate 158. The wall plate 160 is hanged from the upper cover 112, extended up to the worktop 146 and used for protecting the motor 134. The waste is accordingly prevented from entering between the wall plate 160 and the side wall 116.

There is also provided a space 162 in the radial outward direction of the fourth fixed blade 140d, the space communicating with a long narrow chamber 164 thereunder in which a screw conveyor 166 is installed. An opening 168 is provided in the outer lower end portion of the chamber 164. While the screw conveyor 166 rotates in the chamber 164, it forces out the crushed waste discharged by the rotors 183 into the space 162 up to the opening 168.

In FIG. 6, numeral 171 refers to a door 171 for use in supplying an antiseptic solution; 174 to a device for displaying the liquid level of the antiseptic solution; and 176 to an antiseptic solution supply port.

In operation, a power supply button on a control panel 170 located on the front cover of the apparatus as shown in FIG. 6 is pressed to rotate the motor 134. Subsequently, the door 122 in the upper cover 112 is opened. The limit switch 126 then actuates but the feed conveyor 132 will not operate even though the switch for actuating the conveyor is turned on. While the conveyor 132 remains stationary, waste to be crushed is deposited. When the switch is turned on after the door 122 is completely closed with the aid of the magnet catch 124, the conveyor 132 starts to operate. As a result, the waste to be crushed on the conveyor 132 is thrown into the inlet 150 for the waste in the crushing unit 136 via the guide plate 158. The wind pressure generated by the rotors 138 rotated by the motor 134 at high speed causes the waste to be sucked into the inlet and guided to the crushing unit 136 where the waste is crushed to pieces between the rotary blades 142 formed on the rotors and the four fixed blades 140 as in the case of the first embodiment. Since the crushed waste is pressed against the bottom face of the crushing unit by the rotors 138, they are kept from spouting out of the inlet 150 during the crushing operation.

In addition, the rotation of the rotary blades 142 generates a high-speed whirl in the crushing unit 136. Consequently, the industrial waste thus crushed to pieces tangentially flows in the crushing unit 136 and moves from the respective openings 152, 154 of the fourth fixed blade 140d and the cylindrical wall 148 up to the space 162 and passes through the discharge opening 168 via the screw conveyor 166 and jumps into a container 172 under the opening 168.

Moreover, an antiseptic agent may be supplied from the tank via the supply device 156 into the crushing unit 136 as occasion demands during the crushing operation.

The crushed material conveyed by the conveyor from the crushing unit 136 and piled up in the container 172 is taken from the discharge chamber 130, burned and/or buried in the ground. Numeral 178 in FIG. 6 designates a member for preventing the crushed material from scattering therein.

Figure 11:
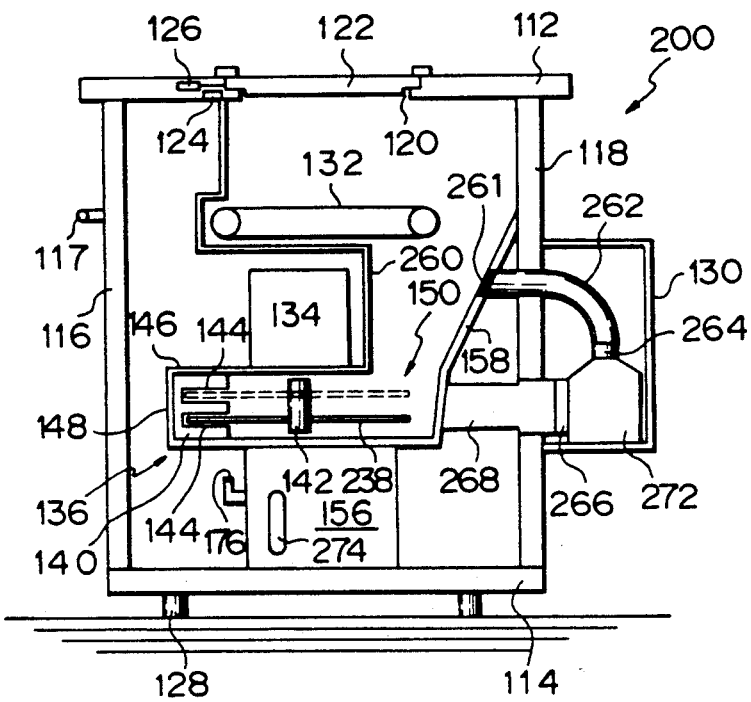
FIG. 11 is an elevational sectional view of an apparatus for disposing of medical waste by crushing according to the present invention as a third embodiment.
Figure 12:
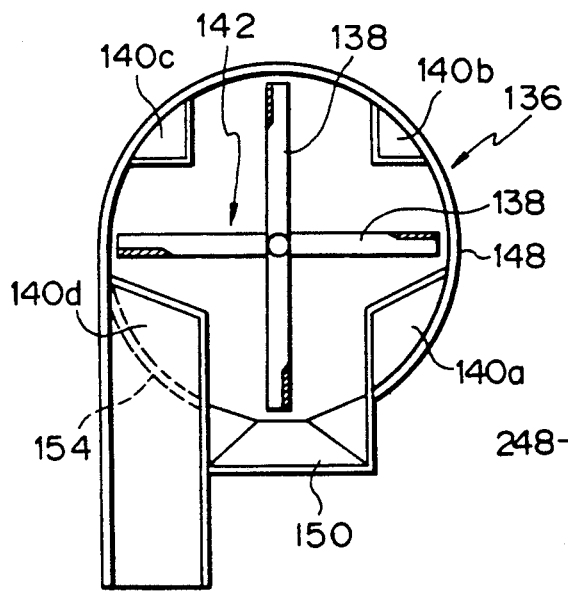
FIG. 12 is a diagram of the internal construction of the crushing unit of FIG. 11 for disposing waste by crushing.
Figure 13:
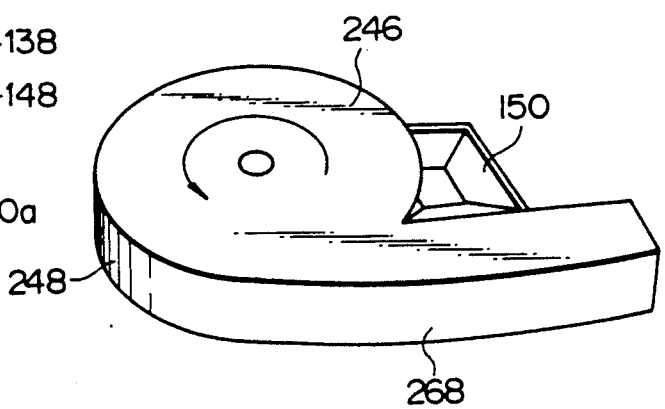
FIG. 13 is a top perspective view of the crushing unit.

FIGS. 11-13 show a third embodiment of the present invention. What makes the third embodiment different from the second embodiment is that a pneumatic discharge unit instead of the screw conveyor 166 in the second embodiment is used as a means of sending crushed pieces out of the crushing unit. Component parts other than the means mentioned above are substantially similar. In the third embodiment, like reference characters are accordingly given to like component parts of the second embodiment and a description will be given of the difference therebetween.

FIG. 11 is a schematic sectional view of an apparatus 200 similar to what has been shown in FIG. 7 for disposing of medical waste by crushing according to the present invention as a third embodiment.

Unlike the second embodiment, one end of a return duct 262 is coupled via a meshed portion 261 to part of a guide plate 158. The other end of the duct 262 is coupled to a discharge port 264 above a cyclonic discharge port 264 located thereabove. On the other hand, the opening 154 provided in the cylindrical wall 148 is coupled via a pipe 268 to a cyclonic side outlet 266.

The crushing unit 136 operates in the same manner as that in the second embodiment to crush medical waste successively with the rotary blades 142 and the fixed blades 140.

Further, the rotation of the rotary blades 142 generates high-speed whirl in the crushing unit 136. As a result, the crushed industrial waste is caused to flow in the tangentially direction of the crushing unit 136 and sent from the opening 152 (FIG. 10) of the fourth fixed blade 140d and the opening 154 of the cylindrical wall 148 via the pipe 268 to a container 272. The air together with the crushed waste sent to the container 272 is returned via the return duct 262 to the sucking hopper and the inlet 150. As a result, there is formed an air passage from the crushing unit 136 to the pipe 268, the discharge chamber 130, and the return duct 162 up to the inlet 150.

In addition, an antiseptic solution may be supplied from the tank and the supply unit 156 to the crushing unit 136 as occasion demands during the crushing operation as in the case of the second embodiment.

The crushed waste pneumatically transferred from the crushing unit 136 and stored in the container 272 is taken from the discharge chamber 130 before being burnt and/or buried in the ground.

The crushing operation for completing the work of crushing and dumping waste continues only for approximately three minutes. The termination of the work can be sensed without fail from the rotational sound of the rotors. However, a window may be bored in a suitable position of the wall, if necessary. After the completion of the crushing and piling work, it becomes possible to feed the next lot of waste.

According to the present invention, waste products such as used hypodermic needles, most of which have been rendered disposable, glassware for testing purposes and the like can be processed indoors quickly without transferring it to an outdoor incinerator and simply disposed of each time they are produced. In other words, it is unnecessary to accumulate waste products in any one of the depots. This advantage obviates any risk accompanying the transportation of waste devices to outdoor depots, ensures effective use of indoor spaces, and allays the anxiety aroused from the storage of unprocessed devices which may help, e.g. growth, denaturation or leakage of bacteria.

According to the present invention, waste devices are crushed to powder for approximately three minutes and sterilized as occasion demands. The ex post facto process of, e.g. burning and/or burning the crushed waste is greatly facilitated. Since hypodermic needles and the like are broken or completely smashed and glassware is crushed to pieces, no secondary disaster is brought about.

According to the present invention, plastic needles, FR bottles, Ringer's containers and the like in addition to the aforementioned hypodermic needles and glassware are crushed to fine pieces, so that their disposal can be made completely with certainty. In other words, the apparatus for disposing of medical devices according to the present invention ensures that the infection of an apriority immunity anergy syndrome, B-type hepatitis and the like constituting a serious social problem is effectively prevented.

The apparatus 200 in the third embodiment is designed to transfer crushed industrial waste without containing liquids such as residual oil, blood, water and the like therein to the disposal container quickly and reliably. If, however, the waste contains various kinds of residual liquid, the crushed material may become sticky and consequently become hardly disposable with ease. Especially when hypodermic needles bearing blood are crushed, the crushed devices may hardly be disposed by air into the disposal container with ease as they become sticky to each other.

In such a case, the second embodiment may be used to convey and force out the crushed industrial waste up to the disposal container by means of the screw conveyor, whereby the apparatus is prevented from being clogged with the crushed waste being conveyed.

In case medical waste devices having diversified shapes and dimensions are to be disposed at one time, they may become tangled with each other and therefore intermittently conveyed by the feed conveyor from the hopper to the crushing unit. As a result, a large amount of waste is supplied to the crushing unit, which may cause trouble in crushing them. This phenomenon often occurs when waste material is made to fall from the hopper onto the feed conveyor and conveyed horizontally. Particularly when the waste contains residual liquid and blood, it may be conveyed intermittently as in the cases of the second and third embodiments. Since the provision of such conveyor tends to make the crushing unit large in size, the conveyor is dispensed with in the first embodiment so as to supply the waste from the hopper to the crushing unit by means of the tilted passage. In this way, waste devices are prevented from tangling with each other. More specifically, the crusher chamber 42 is incorporated with the tilted guide passage, so that the crushed waste is allowed to fall down along the guide passage continuously at all times. Even if various kinds of medical devices to be disposed of are deposited at a time, they are prevented from tangling with each other. Consequently, these medical devices in the form of a dumpling are prevented from entering the shredder section to ensure that the crushing operation is continuously performed. Since the blades in the crusher chamber are provided within the tilted guide passage, even the waste material brought into contact with the center of rotation of the rotary blades is caused to fall down along the tilted surface and crushed thereby with certainty. As a belt conveyor is made dispensable, the apparatus therefor can be rendered compact, whereas it is equipped with an increased number of rotary blades. Crushing efficiency is thus improved.

What is claimed is:

1. Apparatus for reducing medical waste comprising:
   (a) a housing defining an interior space and a top opening in the housing communicating with said interior space for receiving waste,
   (b) means for conveying the waste generally horizontally toward one side of the housing interior space,
   (c) said interior space defining a crusher chamber, said chamber having top and bottom parallel walls and an arcuate side wall,
   (d) at least two sets of rotor blades in said chamber and means for rotating said blades on an axis oriented perpendicular said parallel walls, said rotor blade sets being arranged in at least two axially spaced sets,
   (e) stator blades cooperating with said rotor blades and comprising circumaxially spaced blocks secured to said arcuate wall,
   (f) said interior space further including a discharge passageway communicating with an opening in said arcuate wall of said crusher chamber to receive the crushed waste and to direct the crushed waste into a removable receptacle provided in the housing adjacent the bottom wall of the housing,
   (g) said means for conveying the waste material horizontally toward one side of the housing interior space includes an inclined guide surface oriented at approximately 60 degrees with respect to the horizontal, said top wall of said crusher chamber being so oriented relative to said guide surface that the axis of rotation of said rotor blades forms only a small or slight angle with respect to said guide surface.

2. Apparatus according to claim 1 further characterized by means for supplying a fluid antiseptic solution to the waste as the waste is so moved horizontally prior to entry into the crusher chamber.

3. Apparatus according to claim 2 wherein a door is provided for selectively closing the top opening into which the medical waste is deposited, and door locking means provided to prevent rotation of said rotor blades when said door is in a position other than its closed position.

4. Apparatus according to claim 2 wherein said blades are designed to achieve movement of the waste material and of the air surrounding such material so as to achieve a pneumatic transfer of the crushed waste toward the discharge portion of the interior space as defined above.

5. Apparatus according to claim 2 wherein said crusher chamber further includes a waste inlet portion for directing material moving horizontally toward one side of the housing and into a peripheral portion of said arcuate wall of said crusher chamber spaced from said discharge passageway and adjacent the chamber top wall.

6. Apparatus according to claim 5 wherein said circumaxially spaced blocks comprise generally E-shaped devices with slots for receiving the tips of said rotor blades, said rotor blades comprising a plurality of generally diametrically extending circumaxially spaced individual cutting blades with said blade tips adapted to pass through the slots of said E-shaped blocks.

7. Apparatus according to claim 6 wherein each of said blocks comprises a generally triangular element, each block having an arcuate wall secured to the arcuate wall of said crusher chamber, and with leading and trailing faces defining said openings for so receiving the rotor blade tips.

8. Apparatus for reducing medical waste comprising:
(a) a housing defining an interior space and a top opening in the housing communicating with said interior space for receiving waste,
(b) means for conveying the waste generally horizontally toward one side of the housing interior space,
(c) said interior space defining a crusher chamber, said chamber having top and bottom parallel walls, and an arcuate side wall,
(d) at least two sets of rotor blades in said chamber and means for rotating said blades on an axis oriented perpendicular said parallel crusher chamber top and bottom walls, said rotor blade sets being arranged in at least two axially spaced sets,
(e) stator blades cooperating with said rotor blades and comprising circumaxially spaced blocks secured to said arcuate wall,
(f) said interior space further including a discharge passageway communicating with an opening in said arcuate wall of said crusher chamber to receive the crushed waste and to direct the crushed waste into removable receptacle provided in the housing adjacent the bottom wall of the housing,
(g) said means for horizontally conveying waste material toward one side of the housing comprising a belt conveyor with an upper run moving generally horizontally toward one side of said housing interior space, and said crusher chamber provided generally below said horizontal conveyor and generally horizontally opposite said discharge passageway whereby to provide a very compact apparatus occupying a minimum of floor space.

9. Apparatus according to claim 8 wherein said blades are designed to achieve movement of the waste material and of the air surrounding such material so as to achieve a pneumatic transfer of the crushed waste toward the discharge portion of the interior space as defined above.

10. Apparatus according to claim 9 wherein a door is provided for selectively closing the top opening into which the medical waste is deposited, and door locking means provided to prevent rotation of said rotor blades when said doors are in a position other than its closed position.

11. The apparatus according to claim 10 wherein said crusher chamber further includes a waste inlet portion for directing material moving horizontally toward one side of the housing into a peripheral portion of said arcuate wall of said crusher chamber that is spaced from said discharge passageway and that is adjacent the chamber top wall.

12. The apparatus according to claim 11 wherein an auger is provided in the discharge passageway associated with said crusher chamber to forcibly direct the crushed waste toward an outlet associated with said removable receptacle.

13. The apparatus according to claim 12 further characterized by casters in the bottom of said housing to facilitate repositioning of the apparatus from location to another.

14. The apparatus according to claim 13 wherein the circumaxially spaced blocks comprise generally E shaped devices with slots for receiving the tips of said rotor blades, said rotor blades comprising a plurality of generally diametrically extending circumaxially spaced individual cutting blades with said blade tips adapted to pass through the slots of said E shaped blocks, the axis of rotation of said blades being oriented generally vertically.

15. The apparatus according to claim 14 wherein each of said blocks comprises a generally triangular element, each such block having an arcuate wall secured to the arcuate wall of said crusher chamber, and with leading and trailing faces defining openings for said slots receiving the rotor blade tips.

16. Apparatus for reducing medical waste comprising:
(a) a housing defining an interior space and a top opening in the housing communicating with said interior space for receiving the waste,
(b) means for conveying the waste material toward one side of the housing and including an inclined guide surface oriented at an angle to the horizontal,
(c) said interior space defining a crusher chamber, said chamber having top and bottom parallel walls and an arcuate side wall,
(d) at least two sets of rotor blades in said chamber and means for rotating said blades on an axis that is also inclined with respect to the horizontal,
(e) stator blades cooperating with said rotor blades and comprising circumaxially spaced blocks secured to said arcuate side wall,
(f) said interior space further including a discharge passageway communicating with an opening in said arcuate wall of said crusher chamber for receiving the crushed waste and directing the crushed waste into a removable receptacle provided in the housing adjacent the bottom wall of the housing,
(g) said inclined guide surface oriented at approximately 60 degrees with respect to the horizontal, and said axis of rotation of said rotor blades oriented at an angle slightly greater than the angle of said inclined guide surface relative to the horizontal.

17. Apparatus according to claim 16 wherein a door is provided for selectively closing the top opening into which the medical waste is deposited, and door locking means provided to prevent rotation of said rotor blades when said door is in a position other than its closed position.

18. Apparatus according to claim 16 wherein said blades are designed to achieve movement of the waste material and of the air surrounding such material in order to achieve a pneumatic transfer of the crushed waste toward the discharge portion of the interior space.

19. The combination according to claim 16 wherein said crusher chamber further includes a waste inlet portion for directing material moving along said guide surface into a peripheral portion of said arcuate wall of said crusher chamber which arcuate crusher chamber wall is spaced from said discharge passageway and is located adjacent the chamber top wall.

* * * * *